United States Patent [19]

Wilk

[11] Patent Number: 5,273,051
[45] Date of Patent: Dec. 28, 1993

[54] METHOD AND ASSOCIATED DEVICE FOR OBTAINING A BIOPSY OF TISSUES OF AN INTERNAL ORGAN

[76] Inventor: Peter J. Wilk, 185 W. End Ave., New York, N.Y. 10023

[21] Appl. No.: 33,107

[22] Filed: Mar. 16, 1993

[51] Int. Cl.⁵ .............................................. A61B 10/00
[52] U.S. Cl. .................... 128/751; 128/753; 128/749; 604/264; 604/272
[58] Field of Search ............... 128/751, 753, 754, 749, 128/750; 604/264, 272

[56] References Cited

U.S. PATENT DOCUMENTS

| | | | |
|---|---|---|---|
| 4,667,684 | 5/1987 | Leigh | 128/754 |
| 4,924,878 | 5/1990 | Nottke | 128/754 |
| 4,966,162 | 10/1990 | Wang | 128/750 |
| 5,048,538 | 9/1991 | Terwilliger et al. | 128/754 |
| 5,201,323 | 4/1993 | Vermeulen | 128/749 |

*Primary Examiner*—William E. Kamm
*Assistant Examiner*—Brian M. Green
*Attorney, Agent, or Firm*—R. Neil Sudol; Henry D. Coleman

[57] ABSTRACT

In a method for obtaining a biopsy of tissues of an internal organ of a patient, such as a liver or spleen, an incision is formed in a blood vessel of the vascular system of the patient and a biopsy device including a flexible elongate tubular member and a biopsy-taking component at a distal end of the tubular member is inserted through the incision into the blood vessel. The biopsy device is manipulated from outside the patient to maneuver the distal end portion of the device through the vascular system to the internal organ. A blood vessel wall in the organ is pierced with a sharp distal tip of the biopsy device upon arrival of the biopsy means at the internal organ. The biopsy device is pushed so that the biopsy-taking component enters the internal organ, the biopsy-taking component being operated to capture a sample of tissues of the internal organ. Subsequently, the biopsy device with the captured tissue sample is removed from the vascular system of the patient through the blood vessel and the incision.

10 Claims, 2 Drawing Sheets

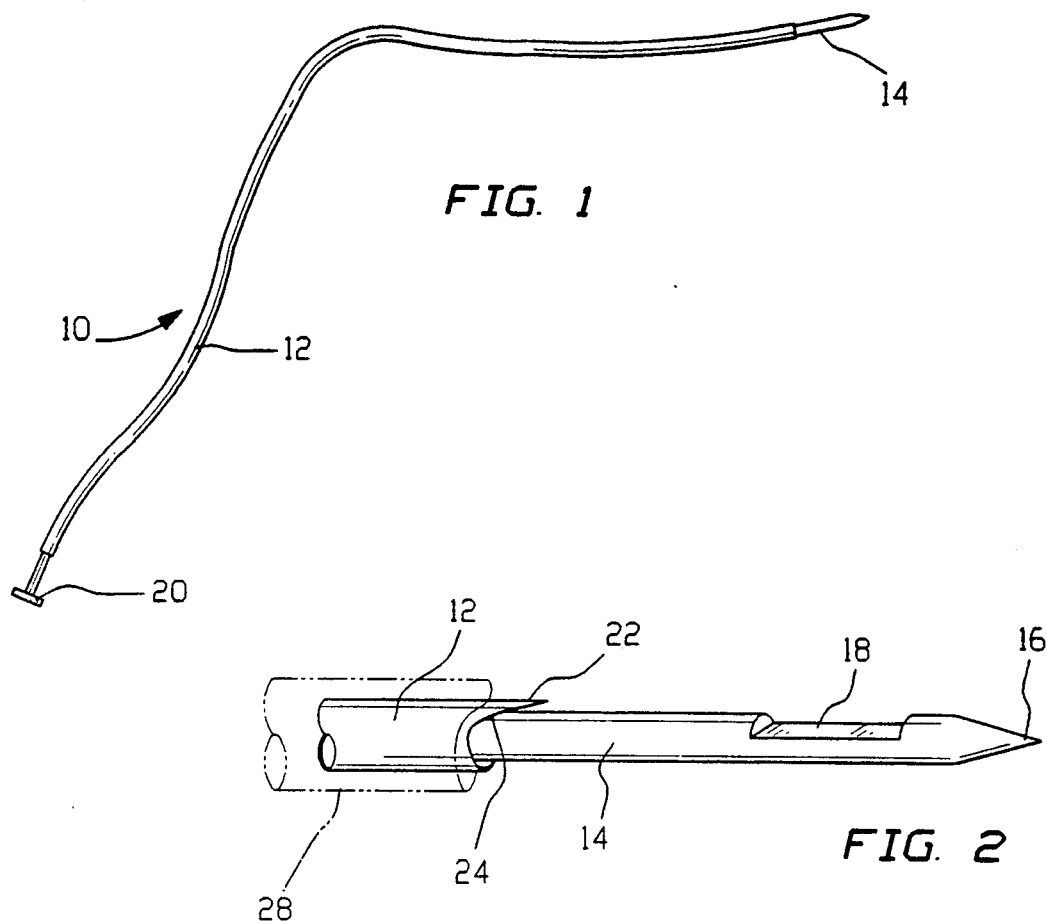
FIG. 1
FIG. 2
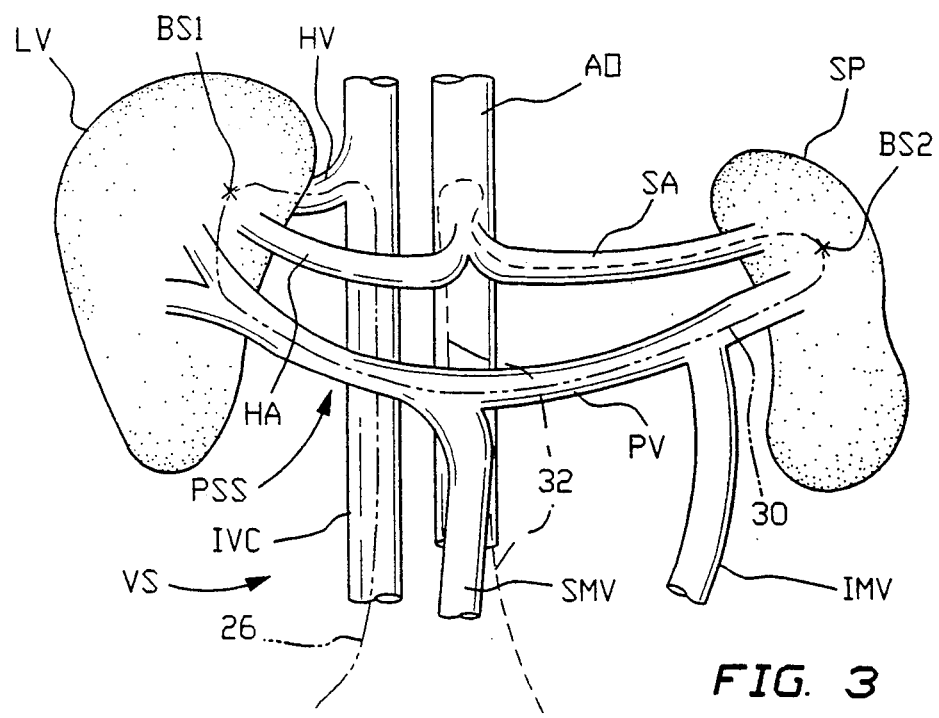
FIG. 3

METHOD AND ASSOCIATED DEVICE FOR OBTAINING A BIOPSY OF TISSUES OF AN INTERNAL ORGAN

BACKGROUND OF THE INVENTION

This invention relates to a method for obtaining a biopsy of tissues of an internal organ of a patient. This invention also relates to an associated device for obtaining a biopsy by the method of the invention. A method and device in accordance with the invention are particularly, but not exclusively, useful in obtaining a biopsy of the liver or the spleen.

A biopsy device currently exists for obtaining tissue samples from internal organs. The device includes a rigid shaft in the form of a rigid tubular member having a sharp distal tip. An elongate rigid rod is inserted through the tubular member, the rod having a sharp distal tip and a recess juxtaposed to the sharp distal tip. An actuator handle is operatively connected to the rod at a proximal end thereof for moving rod relative to the tubular member to insert organic tissues into the recess and subsequently to shear the inserted organic tissues and retain the sheared tissues in the recess.

This biopsy device is marketed under the trademark TRU-CUT and is used by inserting a distal end portion of the device directly into an organ from outside the organ. This insertion can be implemented through overlying tissues. For example, a liver biopsy can be obtained by piercing the abdominal wall of a patient with the sharp distal end of the tubular member, pushing the biopsy device so that the distal end portion of the device passes through the abdominal wall and underlying connective tissues and enters the liver. The rod is then moved in the distal direction relative to the tubular member to thereby expose the recess for receiving liver tissue. Subsequently, the tubular member is shifted distally to cover the recess and thereby shear liver tissues to capture a tissue sample in the recess. Upon capture of the sample, the biopsy device is withdrawn from the patient.

This method for obtaining a tissue sample from the liver has been largely successful but nevertheless suffers from some serious complications or disadvantages. For example, the technique is painful to patients. Moreover, there is a substantial morbidity in the conventional TRU-CUT liver biopsy. The patient can bleed into the abdomen. Usually, liver biopsies are performed on patients who have liver disease including associated coagulation disorders. The liver controls coagulation, particularly with vitamin K and proteins which are essential. Accordingly, a bleeding liver frequently fails to form a clot.

If patient bleeds into the abdomen as a result of a liver biopsy, a transfusion may be required, or even an operation. Operating is dangerous because of the liver disease.

More recently, liver biopsies are taken during a laparoscopic procedure. A laparoscope is used to guide a liver biopsy under direct view. If bleeding occurs, it is controlled by inserting a coagulation device through another laparoscopic trocar sleeve.

If there is bleeding as a result of a liver biopsy in accordance with the present invention, the blood flows directly into the venous system.

Splenic biopsies not possible now. Percutaneous biopsy has a 1% chance of bleeding requiring a splenectomy, which is unacceptable for routine biopsy.

OBJECTS OF THE INVENTION

An object of the present invention is to provide a method for obtaining a biopsy of an internal organ of a patient, such as the liver or spleen.

Another object of the present invention is to provide such a method wherein undesirable bleeding from the biopsy procedure are obviated.

A further object of the present invention is to provide an associated device for use in implementing the method in accordance with the present invention.

These and other objects of the present invention will be apparent from the drawings and detailed descriptions herein.

SUMMARY OF THE INVENTION

A method for obtaining a biopsy of tissues of an internal organ of a patient comprises, in accordance with the present invention, the steps of (a) providing a biopsy device including a flexible elongate tubular member and a biopsy-taking component at a distal end of the tubular member for obtaining a tissue sample, (b) forming an incision in a blood vessel of a vascular system of the patient, (c) inserting a distal end portion of the biopsy device through the incision into the blood vessel, (d) manipulating the biopsy device to maneuver the distal end portion through the vascular system to the internal organ, (e) piercing a blood vessel wall with a sharp distal tip of the biopsy device upon arrival of the biopsy-taking component at the internal organ, (f) pushing the biopsy device so that the biopsy-taking component enters the internal organ, (g) operating the biopsy-taking component to capture a sample of tissues of the internal organ, and (h) withdrawing the biopsy device with the captured tissue sample from the vascular system of the patient through the blood vessel and the incision.

Where the internal organ is the spleen, the blood vessel may be a vein connected to a portal subsystem of the vascular system of the patient. In that event, the method further comprises the step of inserting the distal end portion of the biopsy device through an abdominal wall of the patient prior to the formation of the incision in the blood vessel. More particularly, the blood vessel receiving the incision may be the portal vein, while the distal end portion of the biopsy device is inserted through the abdominal wall of the patient through a laparoscopic trocar sleeve disposed in the abdominal wall of the patient.

Where the blood vessel is a leg vein, the biopsy device is manipulated to insert the distal end portion through the inferior vena cava and the hepatic vein into the liver. Upon arrival of the biopsy-taking component at the liver, a first additional blood vessel wall in the liver is pierced with the sharp distal tip of the biopsy device. The biopsy device is then pushed so that biopsy-taking component at the distal end passes through the first additional blood vessel wall and liver tissues to a second additional blood vessel wall. The second additional blood vessel wall is then pierced with the sharp distal tip of the biopsy device and the biopsy device is pushed so that the biopsy-taking component enters a vein of the portal system through the second additional blood vessel wall. Subsequently, the biopsy device is manipulated to maneuver the distal end portion through a portal vein of the portal system to the spleen.

Where the blood vessel receiving the incision is connected to the aorta of the patient, the manipulation of the biopsy device includes the step of passing the distal end portion of the biopsy device through the aorta and the splenic artery to the spleen.

Where the internal organ is the liver, the distal end portion of the biopsy device may be inserted via a leg vein (e.g., femoral vein) connected to the inferior vena cava. The biopsy device is manipulated to insert the distal end portion through the inferior vena cava and the hepatic vein to the liver. Alternatively, the distal end portion of the biopsy device may be passed to the liver through the aorta and the hepatic artery.

A device for use in obtaining a biopsy of tissues of an internal organ of a patient comprises, in accordance with the present invention, an elongate flexible tubular member and an elongate flexible wire or rod inserted through the tubular member, the wire or rod having a sharp distal tip and a recess juxtaposed to the sharp distal tip. An actuator is operatively connected to the wire or rod at a proximal end thereof for moving the wire or rod relative to the tubular member to insert organic tissues into the recess and subsequently to shear the inserted organic tissues and retain the sheared tissues in the recess.

A method in accordance with the present invention for obtaining a biopsy of a liver eliminates undesirable bleeding from the biopsy procedure. Any blood flowing from the liver as the result of the biopsy procedure enters directly into the vascular system of the patient and is accordingly automatically collected.

A biopsy procedure in accordance with the present invention also permits routine splenic biopsies with a reduced, if not eliminated, chance of splenectomy.

BRIEF DESCRIPTION OF THE DRAWING

FIG. 1 is a schematic side elevational view, on a reduced scale, of a flexible biopsy device in accordance with the present invention, for use in a method in accordance with the present invention.

FIG. 2 is a schematic perspective view, on an enlarged scale, of a distal end portion of the biopsy device of FIG. 1.

FIG. 3 is a schematic side elevational view of a portion of a human vascular system with a liver and a spleen, showing paths for obtaining a biopsy, in accordance with the present invention.

DETAILED DESCRIPTION

Figure 4:
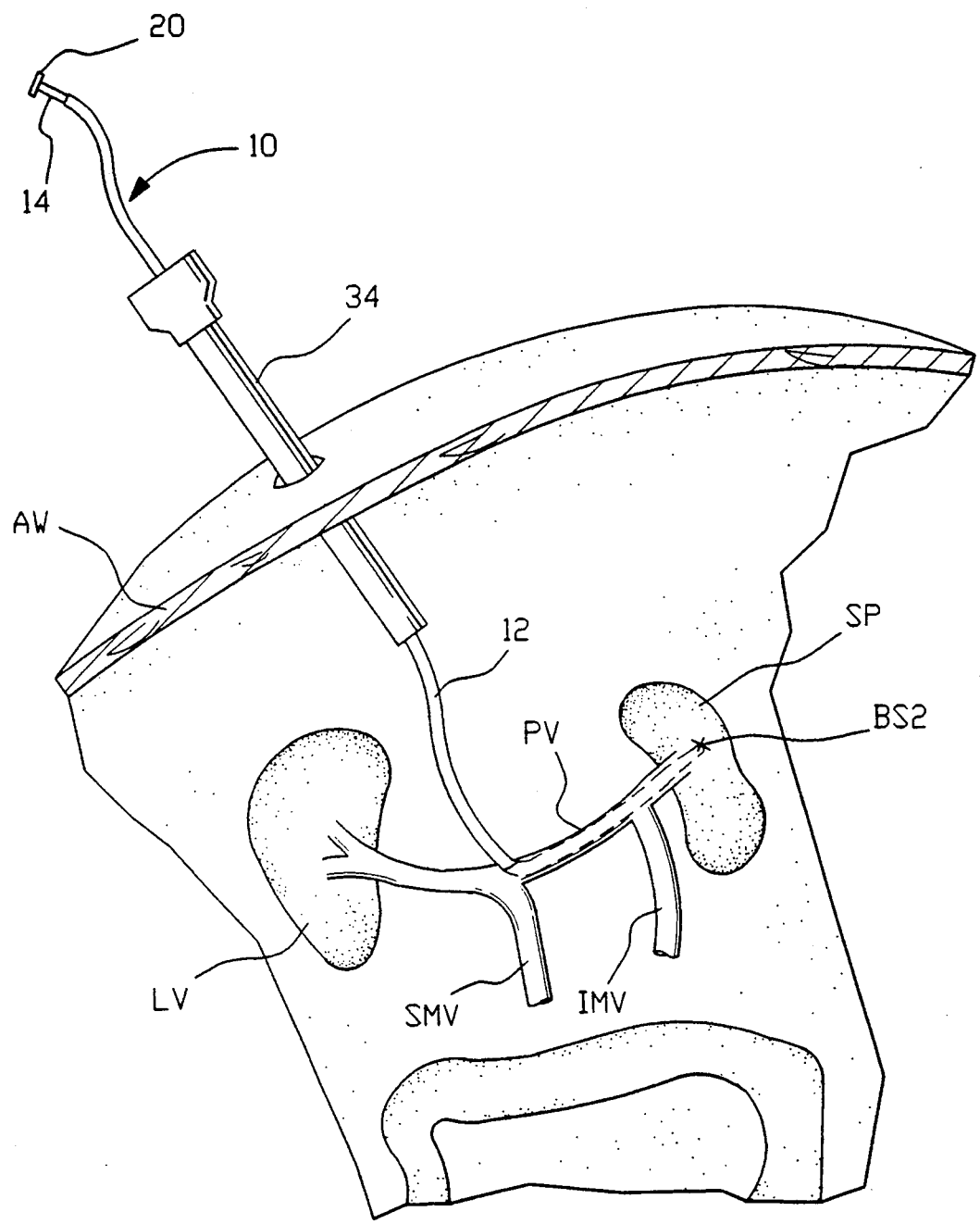
FIG. 4 is a partial schematic cross-sectional view of a human abdomen, showing a laparoscopic biopsy technique in accordance with the present invention.

As illustrated in FIG. 1, a device 10 for use in obtaining a biopsy of tissues of an internal organ of a patient comprises an elongate flexible tubular member 12 having a diameter sufficiently small so that the tubular member can be inserted through bloods vessels of the patient's vascular system to the subject organ. Device 10 further comprises an elongate flexible wire or rod 14 inserted through tubular member 12, the wire or rod having a sharp distal tip 16 and a recess 18 juxtaposed to the sharp distal tip, as shown in FIG. 2.

An actuator such as a knob or flange 20 is operatively connected to rod 14 at a proximal end thereof for moving the wire or rod in a distal direction relative to tubular member 12 to insert organic tissues into recess 18.

Subsequently, tubular member 12 is moved in the distal direction relative to rod 14 to shear the inserted organic tissues and retain the sheared tissues in recess 18. As further shown in FIG. 2, tubular member 12 is formed at a distal tip with a sharp point 22 for facilitating the piercing of a vascular wall and the insertion of the distal end of biopsy device 10 into the tissues of the selected organ, as described in detail hereinafter. Point 22, with its sharpened edges 24, is juxtaposed to recess 18 for facilitating the shearing of tissues inserted into the recess.

To obtain a biopsy of tissues of a liver LV (FIG. 3) of a patient, an incision (not shown) is formed in a blood vessel of a vascular system VS of the patient. Specifically, the incision may be formed in a leg vein of the patient. A distal end portion of biopsy device 10 is then inserted through the incision into the leg vein. Biopsy device 10 is manipulated from outside the patient to maneuver distal end portion of the device through the vascular system to liver LV. More specifically, biopsy device 10 is manipulated from outside the patient to move the distal end portion of the biopsy device through the femoral vein (not shown) and into the inferior vena cava IVC (FIG. 3) along a path 26. During this insertion procedure, recess 18 and sharp distal tip 16 of rod 14 are preferably retracted into the distal end of tubular member 12, to protect the walls of the vascular system from inadvertent injury. To this end, an additional tubular member 28 (FIG. 2) may be provided for shielding point 22. Alternatively, the distal end of tubular member 12 has a sharp circular inside edge and a rounded or blunt circular external edge (not shown), thereby protecting the patient's vessel walls during an insertion procedure, while enabling shearing of a tissue sample captured in recess 18.

Biopsy device 10 is manipulated to turn the distal end of tubular member 12 into the hepatic vein HV. Upon the attainment of a point within liver LV by the distal tip of tubular member 12, a blood vessel wall in the liver is pierced with sharp point 22 or, alternatively, sharp distal tip 16 of biopsy device 10. Biopsy device 10 is then pushed so that the distal end portion of the device, particularly sharp distal tip 16 and recess 18 of rod 14, enters liver LV. Upon a penetration of the distal end of the biopsy device to a desired biopsy site BS1 in the patient's liver LV, the instrument is manipulated so that sharp distal tip 16 and recess 18 are inserted into tissues at the site, while the distal end of tubular member 12 remains outside of biopsy site BS1. Subsequently, tubular member 12 is shifted distally relatively to rod 14, thereby severing a tissue sample in recess 18. The severed tissue sample is maintained in recess 18 by the distal end portion of tubular member 12.

After the capture of the tissue sample, biopsy device 10 is withdrawn with the sample from vascular system VS along the same path 26, i.e., through the hepatic vein HV, the inferior vena cava IVC, and the femoral vein.

FIG. 3 also indicates an insertion path 30 for biopsy device 10 in the event that a biopsy of the spleen SP is desired. Instead of ejecting the distal end portion of rod 14 from tubular member 12 so that recess 18 is exposed, only sharp distal tip 16 is ejected. The protrusion of sharp distal tip 16 from a smooth distal end of tubular member 12 enables not only a piercing of a hepatic blood vessel wall in liver LV, but also a vessel wall in a portal subsystem PSS of vascular system VC upon a passage of the distal end of biopsy device 10 through a portion of the liver. Biopsy device 10 is additionally manipulated to pass the distal end portion of the device through the portal vein PV to the spleen SP, where sharp distal tip 16 pierces a splenic blood vessel wall. Upon a pushing of rod 14 so that recess 18 enters tissues at a biopsy site BS2, tubular member 12 is shifted in a distal direction relative to rod 14 to shear tissues at recess 18 and thereby capture a tissue sample inside recess 18 in the distal end of tubular member 12.

As depicted in FIG. 3, a biopsy of the spleen SP may also be obtained by passing a distal end portion of biopsy device 10 through the aorta AO and into the splenic artery along a path 32 extending from a femoral artery (not shown) to biopsy site BS2 in the spleen.

FIG. 4 illustrates a step in a laparoscopic biopsy procedure wherein biopsy device 10 or a partially rigidified modification thereof is inserted through a trocar sleeve 34 which has been disposed in an abdominal wall AW of a patient pursuant to conventional or equivalent laparoscopic techniques. The distal end portion of biopsy device 10 is inserted from the patient's abdominal cavity AC into portal vein PV through an incision 36 in the vein. Incision 36 is made, for example, by a laparoscopic scalpel device (not shown) inserted through trocar sleeve 34 or a different torcar sleeve (not shown).

FIGS. 3 and 4 also show the superior mesenteric vein SMV and the inferior mesenteric vein connected to the portal vein PV, while FIG. 3 additionally depicts the hepatic artery HA.

Biopsy device 10 is guided through vascular system VS of the patient by known techniques. For example, tubular member 12 may be provided with a catheter-type guidewire (not illustrated) for facilitating the threading of the biopsy device through blood vessels. In addition, radiographic or radio-opaque fluid may be pumped through tubular member 12 to enable X-ray visualization of the progress of the distal end portion of the biopsy device. Tubular member 12 may be provided with tension wires (not shown) for facilitating a turning of the distal end thereof.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for obtaining a biopsy of tissues of an internal organ of a patient, comprising the steps of:
   providing a biopsy device including a flexible elongate tubular member and biopsy means at a distal end of said tubular member for obtaining a tissue sample;
   forming an incision in a blood vessel of a vascular system of the patient;
   inserting a distal end portion of said biopsy device through said incision into said blood vessel;
   manipulating said biopsy device to maneuver said distal end portion through said vascular system to the internal organ;
   upon arrival of said biopsy means at the internal organ, piercing a blood vessel wall with a sharp distal tip of said biopsy device;
   pushing said biopsy device so that said biopsy means enters said internal organ;
   operating said biopsy means to capture a sample of tissues of said internal organ; and
   withdrawing said biopsy device with the captured tissue sample from the vascular system of the patient through said blood vessel and said incision.

2. The method defined in claim 1 wherein said internal organ is the spleen.

3. The method defined in claim 2 wherein said blood vessel is a vein connected to a portal subsystem of the vascular system of the patient, further comprising the step of inserting said distal end portion of said biopsy device through an abdominal wall of the patient prior to said step of forming.

4. The method defined in claim 3 wherein said blood vessel is the portal vein.

5. The method defined in claim 3 wherein the insertion of said distal end portion through the abdominal wall of the patient includes the steps of disposing a laparoscopic trocar sleeve in the abdominal wall of the patient, said distal end portion of said biopsy device being inserted through said trocar sleeve upon disposition thereof in the patient's abdominal wall.

6. The method defined in claim 2 wherein said blood vessel is a leg vein, said step of manipulating including the steps of:
   inserting said distal end portion through the inferior vena cava and the hepatic vein into the liver;
   upon arrival of said biopsy means at the liver, piercing a first additional blood vessel wall in the liver with said sharp distal tip of said biopsy device;
   pushing said biopsy device so that said biopsy means passes through said first additional blood vessel wall and liver tissues to a second additional blood vessel wall;
   piercing said second additional blood vessel wall with said sharp distal tip of said biopsy device;
   pushing said biopsy device so that said biopsy means enters a vein of the portal system through said second additional blood vessel wall; and
   additionally manipulating said biopsy device to maneuver said distal end portion through a portal vein of said portal system to the spleen.

7. The device defined in claim 2 wherein said blood vessel is connected to the aorta of the patient, said step of manipulating including the step of passing said distal end portion of said biopsy device through the aorta and the splenic artery to the spleen.

8. The method defined in claim 1 wherein said internal organ is the liver.

9. The method defined in claim 8 wherein said blood vessel is a leg vein connected to the inferior vena cava, said step of manipulating including the step of inserting said distal end portion through the inferior vena cava and the hepatic vein to the liver.

10. The device defined in claim 8 wherein said blood vessel is connected to the aorta of the patient, said step of manipulating including the step of passing said distal end portion of said biopsy device through the aorta and the hepatic artery to the liver.

* * * * *

UNITED STATES PATENT AND TRADEMARK OFFICE
CERTIFICATE OF CORRECTION

PATENT NO. : 5,273,051
DATED      : December 28, 1993
INVENTOR(S): Peter J. Wilk It is certified that error appears in the above-indentified patent and that said Letters Patent is hereby corrected as shown below:

Column 5:
Claim 1, line 9, change "a" to --said--; delete "portion" and change "biopsy device" to --tubular member--; line 11, change "biopsy device" to --tubular member--; line 12, delete "portion"; line 14, change "biopsy means" to --distal end--; line 17, change "biopsy means" to --distal end--; line 19, change "a" to --said tissue-- and delete "of"; line 20, delete "tissues"; line 21, change "biopsy device" to --distal end--.

Column 6:
Claim 7, line 1, change "device" to --method--.

Claim 10, line 1, change "device" to --method--.

Signed and Sealed this

Seventh Day of June, 1994

*Attest:*

BRUCE LEHMAN

*Attesting Officer*  Commissioner of Patents and Trademarks